(12) United States Patent
Paek (10) Patent No.: US 7,338,764 B2
(45) Date of Patent: Mar. 4, 2008

(54) POLYNUCLEOTIDE MICROARRAY INCLUDING TWO OR MORE GROUPS OF PROBE POLYNUCLEOTIDES IMMOBILIZED ON SUBSTRATE ACCORDING TO MELTING TEMPERATURE AND METHOD FOR DETECTING TARGET POLYNUCLEOTIDES USING THE SAME

(75) Inventor: Sanghyun Paek, Seoul (KR)

(73) Assignee: Samsung Electronics Co., Ltd. (KR)

( * ) Notice: Subject to any disclaimer, the term of this patent is extended or adjusted under 35 U.S.C. 154(b) by 364 days.

(21) Appl. No.: 10/933,178

(22) Filed: Sep. 2, 2004

(65) Prior Publication Data

US 2005/0123951 A1 Jun. 9, 2005

(30) Foreign Application Priority Data

Dec. 3, 2003 (KR) .............. 10-2003-0087166

(51) Int. Cl.
| | |
|---|---|
| C12Q 1/68 | (2006.01) |
| C12M 1/00 | (2006.01) |
| C07H 21/02 | (2006.01) |
| C07H 21/04 | (2006.01) |

(52) U.S. Cl. .............. 435/6; 435/283.1; 536/23.1; 536/24.3

(58) Field of Classification Search .......... 435/6; 536/23.1, 24.3

See application file for complete search history.

(56) References Cited

U.S. PATENT DOCUMENTS

| | | | |
|---|---|---|---|
| 5,143,854 A | 9/1992 | Pirrung et al. | 436/518 |
| 5,424,186 A | 6/1995 | Fodor et al. | 435/6 |
| 5,445,934 A | 8/1995 | Fodor et al. | 435/6 |
| 5,744,305 A | 4/1998 | Fodor et al. | 435/6 |
| 5,871,928 A | 2/1999 | Fodor et al. | 435/6 |
| 2002/0081715 A1* | 6/2002 | Tashiro et al. | 435/287.2 |
| 2003/0152957 A1* | 8/2003 | Shinohara et al. | 435/6 |

FOREIGN PATENT DOCUMENTS

| | | |
|---|---|---|
| CN | 1117161 C | 8/2003 |
| JP | 08166387 | 6/1996 |
| JP | 2002-303626 | 10/2002 |
| JP | 2002303626 | 10/2002 |
| JP | 2003-232791 | 8/2003 |
| WO | 0073766 | 12/2000 |
| WO | WO 01/79548 | 10/2001 |

OTHER PUBLICATIONS

Saiki et al., Analysis of enzymatically amplified β-globin and HLA-DQα DNA with allele-specific oligonucleotide probes. Nature 324: 163-166 (1986).*
DNA Chips and Its Applications, Supervisor: Tadashi Matsunaga, 2000.
Hybridization of Nucleic Acids Immobilized on Solid Supports; Authors: Judy Meinkoth, Geoffrey Wahl; Analytical Biochemistry 138, 267-284; Dated: 1984.
European Search Report for Application EP 0402 1054 dated Sep. 12, 2005.
Korean Intellectual Property Office, Office Action dated Oct. 27, 2005 for Application No. KR 10-2003-0087166, with Explanation of Relevance.
Japanese Office Action dated Mar. 13, 2007 for Application No. 2004-348670 (All references cited in the Office Action, or an English language counterpart of a cited reference, are listed above).
Chinese Office Action dated Jan. 26, 2007 for Application No. 2004100787102.

* cited by examiner

*Primary Examiner*—Ethan Whisenant
(74) *Attorney, Agent, or Firm*—Cantor Colburn LLP (57) ABSTRACT

Provided is a polynucleotide microarray including two or more groups of spots on which probe polynucleotides are immobilized, wherein the probe polynucleotides of each group have melting temperatures (Tms) within a predetermined range of Tm between the probe polynucleotides and target polynucleotides. A method for detecting target polynucleotides using the polynucleotide microarray is also provided.

10 Claims, 1 Drawing Sheet

FIG. 1

SEQUENCE LISTING

```
<160> NUMBER OF SEQ ID NOS: 40

<210> SEQ ID NO 1
<211> LENGTH: 41
<212> TYPE: DNA
<213> ORGANISM: Artificial Sequence
<220> FEATURE:
<223> OTHER INFORMATION: primer

<400> SEQUENCE: 1
taatacgact cactataggg tggccgtgag catcctctgc c            41

<210> SEQ ID NO 2
<211> LENGTH: 40
<212> TYPE: DNA
<213> ORGANISM: Artificial Sequence
<220> FEATURE:
<223> OTHER INFORMATION: primer

<400> SEQUENCE: 2
gtaaccctca ctaaagggag cgtgggttgc gtttgcctgc             40

<210> SEQ ID NO 3
<211> LENGTH: 40
<212> TYPE: DNA
<213> ORGANISM: Artificial Sequence
<220> FEATURE:
<223> OTHER INFORMATION: primer

<400> SEQUENCE: 3
taatacgact cactataggg cgtggccctg tggcagccga             40

<210> SEQ ID NO 4
<211> LENGTH: 40
<212> TYPE: DNA
<213> ORGANISM: Artificial Sequence
<220> FEATURE:
<223> OTHER INFORMATION: primer

<400> SEQUENCE: 4
gtaaccctca ctaaagggag ggctcgttag gagctgaggg             40

<210> SEQ ID NO 5
<211> LENGTH: 42
<212> TYPE: DNA
<213> ORGANISM: Artificial Sequence
<220> FEATURE:
<223> OTHER INFORMATION: primer

<400> SEQUENCE: 5
taatacgact cactataggg cccttgctga gcagatcccg tc           42

<210> SEQ ID NO 6
<211> LENGTH: 40
<212> TYPE: DNA
<213> ORGANISM: Artificial Sequence
<220> FEATURE:
```

```
<223> OTHER INFORMATION: primer

<400> SEQUENCE: 6
gtaaccctca ctaaagggag ggatggtgaa gcttccagcc                    40

<210> SEQ ID NO 7
<211> LENGTH: 40
<212> TYPE: DNA
<213> ORGANISM: Artificial Sequence
<220> FEATURE:
<223> OTHER INFORMATION: primer

<400> SEQUENCE: 7
taatacgact cactataggg gcaaggtcag gggaatggac                    40

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8
gtaaccctca ctaaagggac gccgttgtac ctattgcact cc                 42

<210> SEQ ID NO 9
<211> LENGTH: 43
<212> TYPE: DNA
<213> ORGANISM: Artificial Sequence
<220> FEATURE:
<223> OTHER INFORMATION: primer

<400> SEQUENCE: 9
taatacgact cactataggg ggctcatggg tggctatttc tgc                43

<210> SEQ ID NO 10
<211> LENGTH: 42
<212> TYPE: DNA
<213> ORGANISM: Artificial Sequence
<220> FEATURE:
<223> OTHER INFORMATION: primer

<400> SEQUENCE: 10
gtaaccctca ctaaagggac gtgtcccttg tccccacata cc                 42

<210> SEQ ID NO 11
<211> LENGTH: 42
<212> TYPE: DNA
<213> ORGANISM: Artificial Sequence
<220> FEATURE:
<223> OTHER INFORMATION: primer

<400> SEQUENCE: 11
taatacgact cactataggg tgctgaggca ggacactgct tc                 42

<210> SEQ ID NO 12
<211> LENGTH: 42
<212> TYPE: DNA
<213> ORGANISM: Artificial Sequence
<220> FEATURE:
<223> OTHER INFORMATION: primer

<400> SEQUENCE: 12
gtaaccctca ctaaagggat acaagcaagg acactcacca gc                 42
```

```
<210> SEQ ID NO 13
<211> LENGTH: 41
<212> TYPE: DNA
<213> ORGANISM: Artificial Sequence
<220> FEATURE:
<223> OTHER INFORMATION: primer

<400> SEQUENCE: 13
taatacgact cactataggg cccggacaca gcttggcttc c                    41

<210> SEQ ID NO 14
<211> LENGTH: 42
<212> TYPE: DNA
<213> ORGANISM: Artificial Sequence
<220> FEATURE:
<223> OTHER INFORMATION: primer

<400> SEQUENCE: 14
gtaaccctca ctaaagggaa tccccaccag cttaccgatg ac                   42

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
taatacgact cactataggg caggcctggc ctccacgcag                      40

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
gtaaccctca ctaaagggag gggctctgca gctgagccat                      40

<210> SEQ ID NO 17
<211> LENGTH: 41
<212> TYPE: DNA
<213> ORGANISM: Artificial Sequence
<220> FEATURE:
<223> OTHER INFORMATION: primer

<400> SEQUENCE: 17
taatacgact cactataggg ggcccagtac acccacacgg g                    41

<210> SEQ ID NO 18
<211> LENGTH: 40
<212> TYPE: DNA
<213> ORGANISM: Artificial Sequence
<220> FEATURE:
<223> OTHER INFORMATION: primer

<400> SEQUENCE: 18
gtaaccctca ctaaagggag ggcagggaca gtaagggagg                      40

<210> SEQ ID NO 19
<211> LENGTH: 41
<212> TYPE: DNA
<213> ORGANISM: Artificial Sequence
<220> FEATURE:
<223> OTHER INFORMATION: primer
```

```
<400> SEQUENCE: 19
taatacgact cactataggg gccttgtttg cctctgcagt g                    41

<210> SEQ ID NO 20
<211> LENGTH: 41
<212> TYPE: DNA
<213> ORGANISM: Artificial Sequence
<220> FEATURE:
<223> OTHER INFORMATION: primer

<400> SEQUENCE: 20
gtaaccctca ctaaagggag gccatctggg tggagatgaa g                    41

<210> SEQ ID NO 21
<211> LENGTH: 11
<212> TYPE: DNA
<213> ORGANISM: Artificial Sequence
<220> FEATURE:
<223> OTHER INFORMATION: probe polynucleotide

<400> SEQUENCE: 21
gggagtcctg c                                                     11

<210> SEQ ID NO 22
<211> LENGTH: 11
<212> TYPE: DNA
<213> ORGANISM: Artificial Sequence
<220> FEATURE:
<223> OTHER INFORMATION: probe polynucleotide

<400> SEQUENCE: 22
ggaagtcctg c                                                     11

<210> SEQ ID NO 23
<211> LENGTH: 12
<212> TYPE: DNA
<213> ORGANISM: Artificial Sequence
<220> FEATURE:
<223> OTHER INFORMATION: probe polynucleotide

<400> SEQUENCE: 23
ccaacacctc aa                                                    12

<210> SEQ ID NO 24
<211> LENGTH: 12
<212> TYPE: DNA
<213> ORGANISM: Artificial Sequence
<220> FEATURE:
<223> OTHER INFORMATION: probe polynucleotide

<400> SEQUENCE: 24
ccaacgcctc aa                                                    12

<210> SEQ ID NO 25
<211> LENGTH: 12
<212> TYPE: DNA
<213> ORGANISM: Artificial Sequence
<220> FEATURE:
<223> OTHER INFORMATION: probe polynucleotide

<400> SEQUENCE: 25
acccagaacc cc                                                    12

<210> SEQ ID NO 26
<211> LENGTH: 12
```

```
<212> TYPE: DNA
<213> ORGANISM: Artificial Sequence
<220> FEATURE:
<223> OTHER INFORMATION: probe polynucleotide

<400> SEQUENCE: 26
acccagagcc cc                                                            12

<210> SEQ ID NO 27
<211> LENGTH: 12
<212> TYPE: DNA
<213> ORGANISM: Artificial Sequence
<220> FEATURE:
<223> OTHER INFORMATION: probe polynucleotide

<400> SEQUENCE: 27
ctgccggcat cc                                                            12

<210> SEQ ID NO 28
<211> LENGTH: 12
<212> TYPE: DNA
<213> ORGANISM: Artificial Sequence
<220> FEATURE:
<223> OTHER INFORMATION: probe polynucleotide

<400> SEQUENCE: 28
ctgccagcat cc                                                            12

<210> SEQ ID NO 29
<211> LENGTH: 14
<212> TYPE: DNA
<213> ORGANISM: Artificial Sequence
<220> FEATURE:
<223> OTHER INFORMATION: probe polynucleotide

<400> SEQUENCE: 29
gagatgaagg tctc                                                          14

<210> SEQ ID NO 30
<211> LENGTH: 14
<212> TYPE: DNA
<213> ORGANISM: Artificial Sequence
<220> FEATURE:
<223> OTHER INFORMATION: probe polynucleotide

<400> SEQUENCE: 30
gagatgaaga tctc                                                          14

<210> SEQ ID NO 31
<211> LENGTH: 14
<212> TYPE: DNA
<213> ORGANISM: Artificial Sequence
<220> FEATURE:
<223> OTHER INFORMATION: probe polynucleotide

<400> SEQUENCE: 31
tggtgggccg cctc                                                          14

<210> SEQ ID NO 32
<211> LENGTH: 14
<212> TYPE: DNA
<213> ORGANISM: Artificial Sequence
<220> FEATURE:
<223> OTHER INFORMATION: probe polynucleotide

<400> SEQUENCE: 32
```

```
tggtggagcg cctc                                              14

<210> SEQ ID NO 33
<211> LENGTH: 12
<212> TYPE: DNA
<213> ORGANISM: Artificial Sequence
<220> FEATURE:
<223> OTHER INFORMATION: probe polynucleotide

<400> SEQUENCE: 33
cgggccgccc tg                                                12

<210> SEQ ID NO 34
<211> LENGTH: 12
<212> TYPE: DNA
<213> ORGANISM: Artificial Sequence
<220> FEATURE:
<223> OTHER INFORMATION: probe polynucleotide

<400> SEQUENCE: 34
cgggccaccc tg                                                12

<210> SEQ ID NO 35
<211> LENGTH: 16
<212> TYPE: DNA
<213> ORGANISM: Artificial Sequence
<220> FEATURE:
<223> OTHER INFORMATION: probe polynucleotide

<400> SEQUENCE: 35
caaccggcgc aaagaa                                            16

<210> SEQ ID NO 36
<211> LENGTH: 13
<212> TYPE: DNA
<213> ORGANISM: Artificial Sequence
<220> FEATURE:
<223> OTHER INFORMATION: probe polynucleotide

<400> SEQUENCE: 36
accggcacaa aga                                               13

<210> SEQ ID NO 37
<211> LENGTH: 15
<212> TYPE: DNA
<213> ORGANISM: Artificial Sequence
<220> FEATURE:
<223> OTHER INFORMATION: probe polynucleotide

<400> SEQUENCE: 37
cccccagtaa ggtcc                                             15

<210> SEQ ID NO 38
<211> LENGTH: 15
<212> TYPE: DNA
<213> ORGANISM: Artificial Sequence
<220> FEATURE:
<223> OTHER INFORMATION: probe polynucleotide

<400> SEQUENCE: 38
cccccagtaa aggtc                                             15

<210> SEQ ID NO 39
<211> LENGTH: 13
<212> TYPE: DNA
<213> ORGANISM: Artificial Sequence
```

-continued

```
<220> FEATURE:
<223> OTHER INFORMATION: probe polynucleotide

<400> SEQUENCE: 39
ccggcccacc ggc                                                          13

<210> SEQ ID NO 40
<211> LENGTH: 13
<212> TYPE: DNA
<213> ORGANISM: Artificial Sequence
<220> FEATURE:
<223> OTHER INFORMATION: probe polynucleotide

<400> SEQUENCE: 40
ccggcccacg ggc                                                          13
```

POLYNUCLEOTIDE MICROARRAY INCLUDING TWO OR MORE GROUPS OF PROBE POLYNUCLEOTIDES IMMOBILIZED ON SUBSTRATE ACCORDING TO MELTING TEMPERATURE AND METHOD FOR DETECTING TARGET POLYNUCLEOTIDES USING THE SAME

BACKGROUND OF THE INVENTION

This application claims priority from Korean Patent Application No. 2003-87166, filed on Dec. 3, 2003, in the Korean Intellectual Property Office, the disclosure of which is incorporated herein in its entirety by reference.

1. Field of the Invention

The present invention relates to a polynucleotide microarray including polynucleotides which are immobilized according to a melting temperature (Tm) and a method for detecting target polynucleotides using the same.

2. Description of the Related Art

A microarray is well known in the pertinent art. Examples of the microarray are disclosed in U.S. Pat. Nos. 5,445,934 and 5,744,305. A method of fabricating a microarray using photolithography is generally known. According to a method of fabricating a polynucleotide microarray using photolithography, predetermined regions of a substrate coated with a monomer having a removable protecting group are exposed to an energy source to remove the protecting group. Then, the deprotected monomer is coupled with a monomer having a removable protecting group. Repetition of the above processes produces a polynucleotide microarray. In this case, polynucleotides to be immobilized on the polynucleotide microarray can be prepared by continued extension of polynucleotide monomers. Alternatively, previously synthesized polynucleotides can be immobilized on predetermined regions of the polynucleotide microarray (also called as "spotting technique"). Such fabrication methods for polynucleotide microarrays are illustrated in U.S. Pat. Nos. 5,744,305, 5,143,854, and 5,424,186. The above patent documents about polynucleotide microarrays and fabrication method thereof are incorporated herein in their entireties by reference.

However, probe polynucleotides are randomly immobilized on these conventional polynucleotide microarrays. Furthermore, a single microarray is covered with a cover formed with an inlet and an outlet for a single hybridization solution, and thus, only single hybridization reaction is allowed. Therefore, conventional microarray techniques are silent about immobilization of probe polynucleotides according to Tm and polynucleotide microarrays including a plurality of blocks.

Various methods for detecting target polynucleotides are known. Generally, according to these methods, target polynucleotides are labeled with a detectable marker and then hybridized with probe polynucleotides on a polynucleotide microarray. After the hybridization is completed, the result of hybridization is analyzed. For example, U.S. Pat. No. 5,871,928 discloses a method for detecting hybridization between target polynucleotides and probe polynucleotides, which includes: (a) attaching labels to the target polynucleotides, (b) contacting, under hybridization conditions, the labeled target polynucleotides with a collection of the probe polynucleotides immobilized on known regions of a substrate; and (c) determining the sequences of the probe polynucleotides which hybridize with the target polynucleotides, the collection including at least 100 probes/cm$^2$.

According to the above method, the collection of the probe polynucleotides immobilized on the microarray is used. However, there is no mention about a method of using blocks of immobilized probe polynucleotides that are grouped according to Tm between the probe polynucleotides and target polynucleotides.

SUMMARY OF THE INVENTION

The present invention provides a polynucleotide microarray including probe polynucleotides immobilized on a substrate, in which the probe polynucleotides are grouped according to a melting temperature (Tm) between the probe polynucleotides and target polynucleotides.

The present invention also provides a method for detecting target polynucleotides using the polynucleotide array, in which hybridization is performed using a different hybridization solution according to a block of probe polynucleotides.

According to an aspect of the present invention, there is provided a polynucleotide microarray including two or more groups of spots on which probe polynucleotides are immobilized, wherein the probe polynucleotides of each group have Tms within a predetermined range of Tm between the probe polynucleotides and target polynucleotides.

According to another aspect of the present invention, there is provided a method for detecting target polynucleotides, which includes spotting samples containing the target polynucleotides onto the probe polynucleotides immobilized on the groups of the spots of the polynucleotide microarray, followed by hybridization, wherein at least one group of the spots is treated with a hybridization solution containing a denaturant, a stabilizer, or a mixture thereof, so that the deviation of Tms between the probe polynucleotides immobilized on the groups of the spots and the target polynucleotides is within a predetermined range.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention provides a polynucleotide microarray including two or more groups (hereinafter, also referred to as "blocks") of spots on which probe polynucleotides are immobilized, wherein the probe polynucleotides of each group have melting temperatures (Tms) within a predetermined range of Tm between the probe polynucleotides and target polynucleotides.

As used herein, the term "polynucleotide microarray" indicates an analysis system in which polynucleotide groups are immobilized in a high density on a substrate. As used herein, the term "spots" indicate regions on the microarray where the same polynucleotides are immobilized on a substrate.

In the polynucleotide microarray of the present invention, for example, first, target polynucleotides are selected. Tms between the target polynucleotides and probe polynucleotides for probing them are calculated. Based on the Tm values thus obtained, the probe polynucleotides are grouped. For example, when Tm between specific target polynucleotides and probe polynucleotides is in a range of 30 to 60° C., the probe polynucleotides can be divided into three groups according to the Tm, i.e., 30-40° C., 40-50° C., and 50-60° C. Probe polynucleotides of each group are immobilized on the same region according to the above-described conventional methods for synthesis of polynucleotides on a solid substrate. The probe polynucleotides of each group immobilized on the same region can be covered with a cover having an inlet and an outlet for a corresponding hybridization solution to independently expose each group of the probe polynucleotides to the corresponding hybridization solution. As a result, the region on which each group of the probe polynucleotides is immobilized forms a compartment that can be independently exposed to the corresponding hybridization solution. In the present invention, the difference in Tm between probe polynucleotide groups immobilized on the same block is not particularly limited but is preferably 10° C. or less and more preferably 5° C. or less.

As used herein, the term "melting temperature (Tm)" refers to the temperature at which 50% of double-stranded polynucleotides are separated into single strands under denaturation conditions or 50% of single-stranded polynucleotides are hybridized under hybridization conditions. The Tm can vary according to a used solution, the base composition and length of a polynucleotide sequence, and the concentration of a denaturant and a stabilizer. The Tm can be determined experimentally or calculated using a correlation equation depending on parameters affecting the Tm. For example, the Tm can be calculated by the following Equation:

$$Tm=81.5+16.6 \times \log_{10}M+0.41 \ (\% \ GC)-0.61 \ (\% \ formamide)-500/length \ (bp)$$

wherein M is a molar concentration (mM) of $Na^+$ and % formamide is % (v/v) of formamide (see Meinkoth, J. and Wahl, G.: (1984) Anal. Biochem. 138, 269).

Equations for Tm, like the above Equation, can be selectively used according to a denaturant or a stabilizer contained in a reaction solution. These equations for Tm are easily available by ordinary persons skilled in the art.

When the polynucleotide microarray thus fabricated is used in a method for detecting target polynucleotides, sensitivity and rapidity of the method can be enhanced. For example, in detecting target polynucleotides, when denaturants of different concentrations are contained in hybridization solutions for groups of probe polynucleotides immobilized on the polynucleotide microarray of the present invention, the Tm of a group of probe polynucleotides with high Tm can be adjusted to be close to the Tm of a group of probe polynucleotides with the lowest Tm. Therefore, more probe polynucleotides able to be hybridized at the same temperature can be immobilized on a single microarray. As a result, more target polynucleotides can be detected on a single microarray. Furthermore, a use of a single microarray increases a detection rate.

The present invention also provides a method for detecting target polynucleotides, which includes spotting samples containing the target polynucleotides onto the probe polynucleotides immobilized on the groups of the spots of the polynucleotide microarray of the present invention, followed by hybridization, wherein at least one group of the spots is treated with a hybridization solution containing a denaturant, a stabilizer, or a mixture thereof, so that the deviation of Tms between the probe polynucleotides immobilized on the groups of the spots and the target polynucleotides is within a predetermined range. Preferably, the deviation is in a range of 0 to 5° C., and more preferably 0 to 3° C.

The method of the present invention may further include detecting the result of the hybridization using a fluorescent light. In this case, the target polynucleotides may be labeled with various detectable markers. For example, the markers may be a radioactive material, a fluorescent material, an enzyme, or a ligand. Preferably, the target polynucleotides are labeled with a fluorescent material.

The denaturant as used herein is a material that renders double-stranded polynucleotides labile and is not particularly limited. Preferably, the denaturant is a compound having free electrons that can inactivate hydrogen bonds between polynucleotide bases. For example, the denaturant is selected from the group consisting of formamide, urea, guanidine chloride, dimethylformamide (DMF), and a mixture thereof. The stabilizer as used herein is a compound stabilizing double-stranded polynucleotides and is not particularly limited. Since polynucleotides are generally negatively charged, it is known that a positively charged compound stabilizes double-stranded polynucleotides. Preferably, the stabilizer is a metal salt containing cations such as $Na^+$, $K^+$, $Ca^{2+}$, and $Mg^{2+}$.

In the present invention, the concentration of the denaturant and the stabilizer can be empirically determined by experiments, or alternatively, can be calculated by the above Equation for Tm.

In the present invention, the hybridization temperature may vary according to desired specificity and sensitivity. The hybridization may be carried out at a temperature that is 20-25° C. lower than the Tm, but is not limited thereto.

Hereinafter, the present invention will be described more specifically by Examples. However, the following Examples are provided only for illustrations and thus the present invention is not limited to or by them.

EXAMPLES

Example 1

Fabrication of Polynucleotide Microarray Having Spots Grouped According to Tm

In this Example, as target polynucleotides, there were used a promoter and exons 1-10 of a wild-type HNF-1 α (hepatocyte nuclear factor-1a) gene associated with maturity-onset diabetes of the young (MODY3). Multiple PCR for the 10 target polynucleotides was performed using 10 pairs of primers (SEQ ID NOS: 1-20) (10 pmol for each primer) and gDNA (0.2 µg) derived from human blood as a template (see Table 1). The multiple PCR was performed as the following conditions: initial denaturation at 95° C. for 5 minutes; 30 cycles of denaturation at 95° C. for 30 seconds, annealing at 64° C. for 10 seconds, and extension at 72° C. for 30 seconds; and final extension at 72° C. for 3 minutes. During the PCR, Cy3-dUTP (Amersham Biosciences, Uppsala, Sweden) was added to prepare the target polynucleotides labeled with a fluorescent dye.

TABLE 1

Primers used in amplification of target polynucleotides derived from HNF-1α gene

| Primer | SEQ ID NO. |
|---|---|
| Promoter_forward | 1 |
| Promoter_reverse | 2 |
| Exon1_forward | 3 |
| Exon1_reverse | 4 |
| Exon2_forward | 5 |
| Exon2_reverse | 6 |
| Exon3_forward | 7 |
| Exon3_reverse | 8 |
| Exon4_forward | 9 |
| Exon4_reverse | 10 |
| Exon5_forward | 11 |
| Exon5_reverse | 12 |
| Exon6_forward | 13 |
| Exon6_reverse | 14 |
| Exon7_forward | 15 |
| Exon7_reverse | 16 |
| Exons8,9_forward | 17 |
| Exons8,9_reverse | 18 |
| Exon10_forward | 19 |
| Exon10_reverse | 20 |

Figure 1:
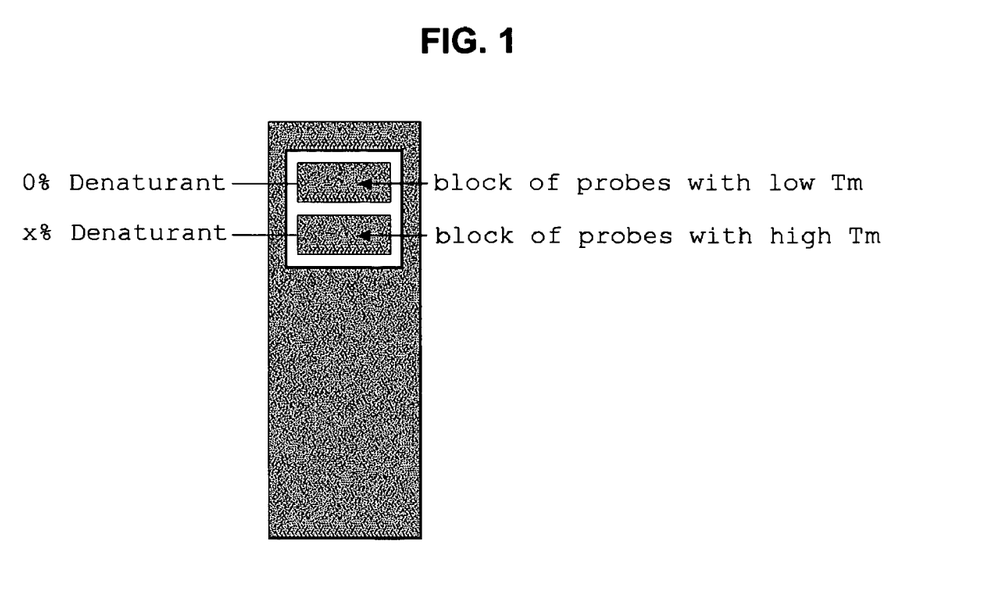
FIG. 1 illustrates an example of a polynucleotide microarray including two blocks according to the present invention.

Probe polynucleotides that are perfectly matched or mismatched with these target polynucleotides were designed. Characteristics of these probe polynucleotides are summarized in Table 2 below. As presented in Table 2, these probe polynucleotides were grouped into two groups, i.e., a group of probe polynucleotides with Tm of 52.8-56.9° C. and a group of probe polynucleotides with Tm of 69.4-77.8° C., and the two groups were respectively immobilized on blocks 1 and 2 (see FIG. 1).

TABLE 2

Sequences and characteristics of probe polynucleotides

| Block | Target site | Completely matched probe (WP) | Mismatched probe (MP) | Tm (° C.) |
|---|---|---|---|---|
| 1 | Exon 1 | SEQ ID NO: 21 | SEQ ID NO: 22 | 55.51 |
| 1 | Exon 2 | SEQ ID NO: 23 | SEQ ID NO: 24 | 54.3 |
| 1 | Exon 7 | SEQ ID NO: 25 | SEQ ID NO: 26 | 52.8 |
| 1 | Exon 9 | SEQ ID NO: 27 | SEQ ID NO: 28 | 56.9 |
| 1 | Exon 10 | SEQ ID NO: 29 | SEQ ID NO: 30 | 53.4 |
| 2 | Exon 1 | SEQ ID NO: 31 | SEQ ID NO: 32 | 77.8 |
| 2 | Exon 2 | SEQ ID NO: 33 | SEQ ID NO: 34 | 71.2 |
| 2 | Exon 4 | SEQ ID NO: 35 | SEQ ID NO: 36 | 71.0 |
| 2 | Exon 4 | SEQ ID NO: 37 | SEQ ID NO: 38 | 69.4 |
| 2 | Exon 9 | SEQ ID NO: 39 | SEQ ID NO: 40 | 75.7 |

The Tm values as presented in Table 2 were calculated by a program (Samsung, Korea) implemented on PERL language using Santa Lucia 98 parameters. These parameters are easily available by ordinary persons skilled in the art.

A polynucleotide microarray according to the present invention was fabricated by a spotting technique using a radial polyethyleneglycol derivative (hydrogel). An illustrative fabrication method of the polynucleotide microarray was as follows.

1. Synthesis of Radial Polyethyleneglycol Derivative with Epoxy Group

Epichlorohydrin (7.5 mL) and tetrabutylammonium bromide (0.32 g) were added to an aqueous solution of NaOH (50 wt %, 2 mL) and stirred. Then, pentaerythritol ethoxylate (1 g) was gradually added thereto and stirred at room temperature for 18 hours. Reaction termination was identified by thin layer chromatography (TLC). When the reaction was not completed, the reaction solution was further stirred at 60° C. for 1 hour. The resultant solution was diluted with water (30 mL) and three times extracted with methylene chloride (40 mL) to obtain an organic layer. The organic layer was three times washed with saturated NaHCO$_3$ (40 mL) and anhydrous MgSO$_4$ was added thereto, followed by drying and removal of a solvent at low pressure. Then, drying was carried out in vacuum for two days to remove an epichlorohydrin residue. As a result, a radial polyethyleneglycol derivative with an epoxy group was obtained and identified by H-NMR and titration of the epoxy group using 0.1 N HBr/acetic acid (glacial).

2. Synthesis of Diamine Crosslinking Agent

Penta(ethyleneglycol)di-tosylate (5 g, 9.2 mmol) was dissolved in dimethylformamide (DMF) (40 mL). NaN$_3$ (4.2 g, 64.1 mmol) and pyridine (0.5 mL) were sequentially added thereto and stirred at 140° C. for 18 hours. A solvent was removed from the reaction solution at a low pressure and water (200 mL) was added with stirring. The reaction solution was extracted with methylene chloride (100 mL) to obtain an organic layer. The organic layer was three times washed with brine (100 mL) and anhydrous MgSO$_4$ was added thereto, followed by drying, removal of a solvent at a low pressure, and flash column chromatography (EA:n-Hex=1:2), to give a diazide intermediate. The diazide intermediate was dissolved in methanol (30 mL), 10% Pd—C (0.1 equivalents) was added, and reduction was performed at a hydrogen atmosphere for 18 hours. A catalyst was removed from the resultant solution using a Celite pad and the Celite pad was washed with ethanol. A resultant filtrate and the ethanol washing solution were mixed, followed by removal of a solvent at a low pressure, to give a diamine crosslinking agent.

3. Preparation of Gel Matrix Solution Using Crosslinking Agent

Polyethylene glycol (PEG) with a molecular weight of 1,500 was added to an aqueous solution of 2N NaOH and stirred in an ice bath to prepare a PEG crosslinking agent solution.

Next, the radial polyethyleneglycol derivative with an epoxy group synthesized in Section 1 was dissolved in a carbonate buffer (0.1 M, pH 9.1). The previously prepared PEG crosslinking agent solution was gradually added thereto and stirred at room temperature for 3 hours. When reaction termination was identified, the resultant solution was extracted with methylene chloride and stored at 4° C. after removal of a solvent at a low pressure.

4. Fabrication of Polynucleotide Microarray by Spotting Gel Matrix-DNA Conjugate Solution on Chips The previously prepared probe polynucleotides were added to the gel matrix solution prepared in Section 3 so that the radial polyethyleneglycol with an epoxy group, the diamine crosslinking agent, and the probe polynucleotides were in an equivalent ratio of 4:1:4, and incubated at 37° C. for 14 hours with stirring, to obtain a matrix-DNA conjugate solution. The matrix-DNA conjugate solution was used as a spotting solution.

The spotting solution was spotted on a glass, which had been surface-treated to have an amine group, and incubated in a wet chamber at 37° C. for 4 hours. Then, to perform background control, i.e., to prevent attachment of the target polynucleotides to the surface of the glass, the glass was surface-treated so that amine groups on the unspotted surface of the glass were negatively charged, and then incubated in a drying machine.

Meanwhile, control polynucleotide microarrays were fabricated. In the control polynucleotide microarrays, probe polynucleotides were immobilized on a substrate without being grouped by Tm so that hybridization was performed under the same hybridization condition.

Example 2

Hybridization and Detection of Target Polynucleotides

A mixture of the 10 region sequences of the wild-type HNF-1 α gene of Example 1 was used for target polynucleotides.

image analysis was carried out using GenePix Pro software (Axon Instruments, America). Fluorescent light was measured at 532 nm.

For control experiments, as described above, polynucleotide microarrays having immobilized probe polynucleotides therein so that hybridization was performed under the same conditions, i.e., polynucleotide microarrays that were not grouped into blocks by Tm were used. Hybridization was performed using a hybridization solution containing no formamide at 32° C. (control 1) and 40° C. (control 2). Other conditions of the controls 1 and 2 were the same.

The results are presented in Table 3 below. Remarks about blocks in Table 3 are applied only for the test group.

TABLE 3

| | Target | Hybridization results | | | | | | | |
|---|---|---|---|---|---|---|---|---|---|
| | | Test group | | | Control 1 | | | Control 2 | | |
| Block | site | Wp | Mp | Ratio | Wp | Mp | Ratio | Wp | Mp | Ratio |
| 1 | Exon 1 | 6712 | 10 | 6.51 | 5924 | 10 | 6.38 | 2962 | 4.5 | 6.49 |
| 1 | Exon 2 | 4934 | 11 | 6.11 | 3850 | 10 | 5.96 | 1925 | 5.9 | 5.79 |
| 1 | Exon 7 | 20021 | 3524 | 1.74 | 18005 | 3348.6 | 1.68 | 9002.5 | 1512 | 1.78 |
| 1 | Exon 9 | 7178.4 | 32 | 5.41 | 6596 | 24.8 | 5.58 | 3298 | 14 | 5.46 |
| 1 | Exon 10 | 14366 | 10 | 7.27 | 14706 | 10 | 7.29 | 7353 | 4.8 | 7.33 |
| 2 | Exon 1 | 2016.4 | 1 | 7.61 | 2833.2 | 56 | 3.92 | 1416.6 | 1 | 7.26 |
| 2 | Exon 2 | 3221.8 | 1 | 8.08 | 5087.2 | 365.8 | 2.63 | 2543.6 | 1 | 7.84 |
| 2 | Exon 4 | 14269.6 | 309.4 | 3.83 | 17842.4 | 1671.8 | 2.37 | 8921.2 | 281 | 3.46 |
| 2 | Exon 4 | 14637 | 262.8 | 4.02 | 14031.8 | 874.4 | 2.78 | 7015.9 | 210 | 3.51 |
| 2 | Exon 9 | 4009 | 1 | 8.30 | 3321.4 | 179.8 | 2.92 | 1660.7 | 1 | 7.41 |

Wp: probe polynucleotides perfectly matched with target polynucleotides
Mp: probe polynucleotides mismatched with target polynucleotides
Ratio: ln(Wp/Mp) value
Test group: block 1; 0% formamide, 32° C., block 2; 7.5% formamide, 32° C.
Control 1: 0% formamide, 32° C.
Control 2: 0% formamide, 40° C.

A hybridization solution containing no formamide was used in the block 1 of the polynucleotide microarray having the two blocks as fabricated in Example 1. On the other hand, a hybridization solution containing 7.5% formamide was used in the block 2.

The multiple PCR products obtained in Example 1 were identified by comparison with a molecular weight marker upon 1.8% agarose gel electrophoresis. The multiple PCR revealed amplification of all of the 10 target gene sites (579, 459, 365, 308, 332, 241, 286, 230, 414, and 171 bp). The PCR products were purified using a PCR product purification kit (Qiagen). The purified DNAs were incubated with 0.5 U DNase I (Boehringer Mannheim, Germany) at 37° C. for 10 minutes and a stop mix was then added for reaction termination. The cut DNA products were adjusted to have a concentration of 150-187.5 nM, denatured at 94° C. for 5 minutes, and incubated over an ice for 2 minutes. The cooled DNA solution was mixed with the same quantity of a hybridization buffer (6×SSPE-0.1% Triton X-100) and then added to a hybridization chamber of the polynucleotide microarray. The microarray was incubated at 32° C. for 16 hours and washed with a washing buffer I (6×SSPE-Triton X-100 0.05%) at room temperature for 5 minutes and then a washing buffer 11 (3×SSPE-Triton X-100 0.005%) at room temperature for 5 minutes. The microarray was dried at room temperature for 15 minutes and scanned (test group). In the scanning, images were created using a GenePix 4000B model scanner (Axon Instruments, America) and As shown in Table 3, the probe polynucleotides immobilized on the block 1 of the test microarray had the same conditions as the control microarray 1. Therefore, there were little differences in fluorescent intensity and ln(Wp/Mp). The fluorescent intensity of the probe polynucleotides immobilized on the block 2 of the test microarray was slightly decreased but ln(Wp/Mp) values were significantly increased, as compared to the control microarray 1. The probe polynucleotides immobilized on the block 2 of the test microarray were enhanced in both fluorescent intensities and ln(Wp/Mp) values, as compared to the control microarray 2. That is, hybridization at the same temperature condition using a microarray having two blocks of polynucleotides immobilized on a substrate can provide the same results as when two microarrays are used.

When hybridization for probe polynucleotides with a broad Tm distribution is performed at a single temperature, a hybridization temperature optimized for one or both of a probe group with low Tm and a probe group with high Tm must be used. As described in this Example, according to the present invention, addition of a denaturant or a stabilizer to a hybridization solution enables hybridization at a single temperature in a single microarray.

As apparent from the above description, the polynucleotide microarray of the present invention includes immobilized probe polynucleotides which are grouped into blocks by Tm. Therefore, the number of target polynucleotides that can be detected using a single microarray and the detection rate can be increased, thereby decreasing detection costs.

Furthermore, the polynucleotide microarray of the present invention can enhance sensitivity and rapidity in detection of target polynucleotides.

According to the method for detecting target polynucleotides of the present invention, the target polynucleotides can be rapidly detected at high sensitivity.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A polynucleotide microarray comprising
two or more groups of spots on which probe polynucleotides are immobilized,
wherein the probe polynucleotides are grouped according to a melting temperature (Tm) in a first hybridization solution between the probe polynucleotides and target polynucleotides, and
wherein probe polynucleotides of each group have melting temperatures (Tms) within a predetermined range; and
a cover for each group of spots,
wherein the cover has an inlet and an outlet, and
wherein the cover and each group of spots can form an individual compartment.

2. The polynucleotide microarray of claim 1, wherein a difference in Tm between the spots of each group is 10° C. or less.

3. The polynucleotide microarray of claim 1, wherein a difference in Tm between the spots of each group is 5° C. or less.

4. A method for detecting target polynucleotides, which comprises
spotting samples containing target polynucleotides onto probe polynucleotides immobilized on each group of spots of a polynucleotide microarray, wherein the polynucleotide microarray comprises
two or more groups of spots on which probe polynucleotides are immobilized,
wherein the probe polynucleotides are grouped according to a melting temperature (Tm) in a first hybridization solution between the probe polynucleotides and target polynucleotides, and
wherein probe polynucleotides of each group have melting temperatures (Tms) in the first hybridization solution within a predetermined range;
treating each group of spots or the samples with a second hybridization solution,
wherein the second hybridization solution for a group of spots comprises a denaturant, a stabilizer, or a mixture thereof, and
wherein the second hybridization solution for a group of spots is selected such that for each probe polynucleotide of the group a difference between a Tm in the second hybridization solution between the probe polynucleotide and the target polynucleotides and a hybridization temperature (T) is within a predetermined range;
hybridizing the target polynucleotides to the probe polynucleotides immobilized on each group of spots at the hybridization temperature (T); and
detecting a result of the hybridization to detect the target polynucleotides.

5. The method of claim 4, wherein the target polynucleotides are labeled with a fluorescent marker and detecting the result of the hybridization uses a fluorescent light.

6. The method of claim 4, wherein the denaturant is selected from the group consisting of formamide, urea, guanidine chloride, dimethylformamide (DMF), and a mixture thereof.

7. The method of claim 4, wherein the stabilizer is a salt selected from the group consisting of $Na^+$, $K^+$, $Ca^{2+}$, and $Mg^{2+}$.

8. The method of claim 4, wherein for each group of spots the difference between the Tms and the hybridization temperature (T) is in a range of 0 to 5° C.

9. The method of claim 4, wherein for each group of spots the deviation of the Tms and the hybridization temperature (T) is in a range of 0 to 3° C.

10. The method of claim 4, wherein each group of spots is covered with a cover,
wherein the cover has an inlet and an outlet, and
wherein the cover and the group of spots form a compartment.

* * * * *